(12) United States Patent
Ho et al.

(10) Patent No.: US 11,865,147 B2
(45) Date of Patent: Jan. 9, 2024

(54) METHODS FOR REDUCING PURINE CONTENT AND ALLEVIATING DISORDER OF URIC ACID METABOLISM

(71) Applicant: GLAC BIOTECH CO., LTD., Tainan (TW)

(72) Inventors: Hsieh-Hsun Ho, Tainan (TW); Ching-Wei Chen, Tainan (TW); Yi-Wei Kuo, Tainan (TW); Jui-Fen Chen, Tainan (TW)

(73) Assignee: GLAC BIOTECH CO., LTD., Tainan (TW)

( * ) Notice: Subject to any disclaimer, the term of this patent is extended or adjusted under 35 U.S.C. 154(b) by 0 days.

(21) Appl. No.: 17/457,758

(22) Filed: Dec. 6, 2021

(65) Prior Publication Data
US 2022/0273734 A1 Sep. 1, 2022

(30) Foreign Application Priority Data

Feb. 26, 2021 (TW) ................................. 110107159

(51) Int. Cl.
| | |
|---|---|
| *A61K 35/747* | (2015.01) |
| *A61P 19/06* | (2006.01) |
| *C12N 1/20* | (2006.01) |
| *C12P 1/04* | (2006.01) |
| *A23L 33/135* | (2016.01) |
| *A23L 33/00* | (2016.01) |
| *C12R 1/25* | (2006.01) |

(52) U.S. Cl.
CPC .......... *A61K 35/747* (2013.01); *A23L 33/135* (2016.08); *A23L 33/40* (2016.08); *A61P 19/06* (2018.01); *C12N 1/205* (2021.05); *C12P 1/04* (2013.01); *A23V 2002/00* (2013.01); *A23V 2400/143* (2023.08); *A23V 2400/169* (2023.08); *A23V 2400/173* (2023.08); *C12R 2001/25* (2021.05)

(58) Field of Classification Search
CPC ..... A61K 35/747; A23L 33/135; A23L 33/40; A23L 29/065; A61P 19/06; A61P 13/04; A61P 13/12; A61P 19/02; C12P 1/04; A23V 2002/00; A23Y 2220/35; A23Y 2220/67; A23Y 2220/71; C12R 2001/25; C12R 2001/225; A23C 9/1234; A23G 3/366; A23K 10/12; A23K 10/18
See application file for complete search history.

(56) References Cited

FOREIGN PATENT DOCUMENTS

| | | | | |
|---|---|---|---|---|
| CN | 104839661 A | * | 8/2015 | ........... A23L 33/135 |
| CN | 108486007 A | * | 9/2018 | ........... A23L 33/135 |
| CN | 111388509 A | | 7/2020 | |

OTHER PUBLICATIONS

Li M, Yang D, Mei L, Yuan L, Xie A, et al. (2014) Screening and Characterization of Purine Nucleoside Degrading Lactic Acid Bacteria Isolated from Chinese Sauerkraut and Evaluation of the Serum Uric Acid Lowering Effect in Hyperuricemic Rats. PLOS ONE 9(9): e105577. (Year: 2014).*

* cited by examiner

*Primary Examiner* — Thomas J. Visone
(74) *Attorney, Agent, or Firm* — Hamre, Schumann, Mueller & Larson, P.C.

(57) ABSTRACT

Disclosed herein are methods for reducing purine content in an edible material and alleviating a disorder of uric acid metabolism using *Lactobacillus plantarum* TSP05 which is deposited at the China General Microbiological Culture Collection Center (CGMCC) under an accession number CGMCC 16710.

8 Claims, 1 Drawing Sheet

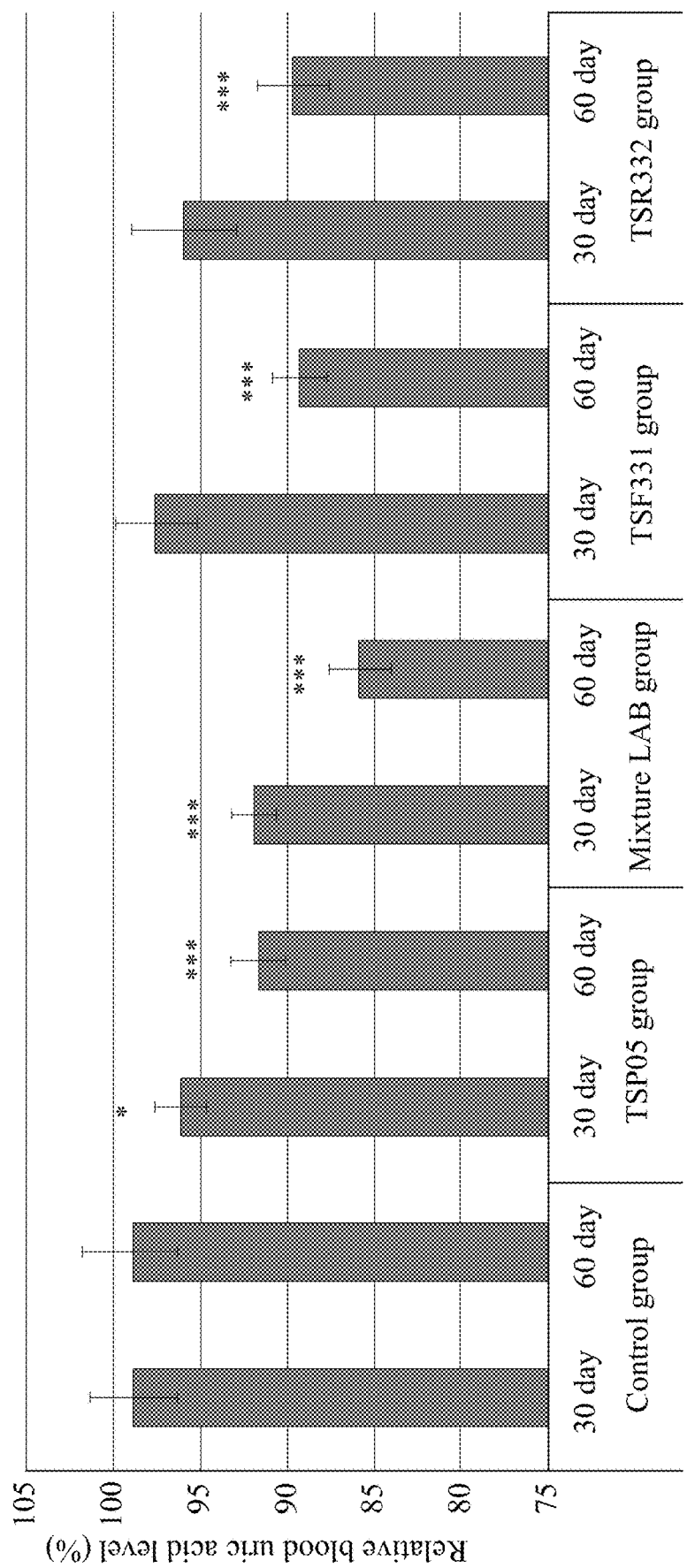

METHODS FOR REDUCING PURINE CONTENT AND ALLEVIATING DISORDER OF URIC ACID METABOLISM

CROSS-REFERENCE TO RELATED APPLICATION

This application claims priority of Taiwanese Invention Patent Application No. 110107159, filed on Feb. 26, 2021.

FIELD

The present disclosure relates to methods for reducing purine content in an edible material and alleviating a disorder of uric acid metabolism using *Lactobacillus plantarum* TSP05.

BACKGROUND

Uric acid is a final oxidation product of purine metabolism, and is excreted from the body in urine through the kidneys. Excessive intake of purine-rich foods such as mushrooms, legumes, meat and seafood can easily lead to abnormalities in uric acid metabolism, including overproduction and/or underexcretion of uric acid, resulting in an increased blood uric acid level, and further giving rise to disorders of uric acid metabolism such as gout, hyperuricemia, etc.

Due to changes in dietary habits nowadays, the incidence and prevalence of disorders of uric acid metabolism are increasing year by year, and such trend is particularly observed among younger individuals. Therefore, approaches to effectively reduce the amount of purines in purine-rich foods and to lower a blood uric acid level so as to treat and/or prevent disorders of uric acid metabolism have become an important research topic.

At present, various known physical or chemical methods (e.g., processing treatment, adsorption treatment, etc.) have been utilized for reducing the amount of purine compounds in food. However, these methods not only involve complicated operating procedures, but also require removal of chemical reagents added. The current drugs used for lowering a blood uric acid level include uricogenesis inhibitors and uricosuric agents. However, in clinical applications, these drugs have problems of providing low efficacy and easily causing side effects.

Lactic acid bacteria (LAB) are gram-positive, lactic acid-producing bacteria that are conferred with the generally recognized as safe (GRAS) status, and are widely used as probiotics. LAB have been reported to exert effects such as inhibiting the growth of pathogens in the gastrointestinal tract, alleviating lactose intolerance, providing anti-cancer properties, lowering blood pressure (i.e., antihypertensive), etc. Examples of common LAB include *Lactobacillus* spp., *Lactococcus* spp., *Pediococcus* spp., *Streptococcus* spp., *Enterococcus* spp., *Bifidobacterium* spp , *Bacillus* spp., *Leuconostoc* spp., etc.

Previous studies have attempted to use certain strains of LAB to degrade purines and to lower blood uric acid levels. For example, the applicant discloses in Chinese Invention Patent Application Publication No. CN 111388509 A that at least one LAB strain selected from the group consisting of *Lactobacillus fermentum* TSF331 (deposited at the China General Microbiological Culture Collection Center (CGMCC) under an accession number CGMCC 15527) and *Lactobacillus reuteri* TSR332 (deposited at the CGMCC under an accession number CGMCC 15528) is able to effectively degrade purines as shown in vitro experiments, and to effectively lower blood uric acid levels as demonstrated in vivo animal testing.

In spite of the aforesaid report, there is still a need to develop a new strategy that can be utilized for reducing purine content in an edible material and alleviating a disorder of uric acid metabolism.

SUMMARY

Therefore, in a first aspect, the present disclosure provides a method for reducing purine content in an edible material which can alleviate at least one of the drawbacks of the prior art.

The method includes cultivating a lactic acid bacterial strain capable of degrading a purine in the edible material. The lactic acid bacterial strain is *Lactobacillus plantarum* TSP05 which is deposited at the China General Microbiological Culture Collection Center (CGMCC) under an accession number CGMCC 16710.

In a second aspect, the present disclosure provides a method for alleviating a disorder of uric acid metabolism, which can alleviate at least one of the drawbacks of the prior art, and which includes administering to a subject in need thereof a composition containing the abovementioned *Lactobacillus plantarum*. TSP05.

BRIEF DESCRIPTION OF THE DRAWINGS

Other features and advantages of the present disclosure will become apparent in the following detailed description of the embodiments with reference to the accompanying drawings, of which:

FIG. 1 shows the relative blood uric acid level of the subjects in each group of Example 2 at day 30 and day 60, infra, in which the symbols "*" and "***" respectively represent $p<0.05$ and $p<0.001$ (compared with the control group).

DETAILED DESCRIPTION

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the word "comprises" has a corresponding meaning.

Unless otherwise defined, all technical and scientific terms used herein have the meaning commonly understood by a person skilled in the art to which this disclosure belongs. One skilled in the art will recognize many methods and materials similar or equivalent to those described herein, which could be used in the practice of this disclosure. Indeed, this disclosure is in no way limited to the methods and materials described.

In the development of active components that can be used to modulate purine metabolism, the applicant surprisingly found that a specific lactic acid bacterial strain is capable of effectively degrading purines in an edible material within a short period of time, and hence is expected to be effective in reducing the content of metabolites and end-products of purine metabolism, such as uric acid.

Therefore, the present disclosure provides a method for reducing purine content in an edible material, including cultivating a lactic acid bacterial strain capable of degrading a purine in the edible material. The lactic acid bacterial strain is *Lactobacillus plantarum* TSP05 which is deposited at the China General Microbiological Culture Collection Center (CGMCC) under an accession number CGMCC 16710.

As used herein, the term "purine content" refers to the content of a compound having a purine skeleton. Examples of the compound having a purine skeleton include, but are not limited to, purine nucleosides (e.g., inosine, guanosine, etc.), purine nucleotides (e.g., inosinic acid, etc.) and nucleic acids.

Examples of the edible material may include, but are not limited to, mushrooms, legumes, meat, offals, seafood, and alcoholic beverages.

As used herein, the term "cultivating" can be used interchangeably with other terms such as "fermentation" and "culturing".

It should be noted that operating conditions for cultivating the lactic acid bacterial strain may be changed according to the purine content of the edible material, the ratio of amount of the edible material to that of the lactic acid bacterial strain, etc., so as to achieve an optimal effect of purine degradation. The choice of these operating conditions can be routinely determined by those skilled in the art.

According to the present disclosure, cultivation of the lactic acid bacterial strain may be performed at a temperature ranging from 35° C. to 37° C.

According to the present disclosure, cultivation of the lactic acid bacterial strain may be performed during or after preparation of the edible material.

In certain embodiments, the method of the present disclosure further includes simultaneously cultivating, in the edible material, *Lactobacillus fermentum* TSF331 and *Lactobacillus reuteri* TSR332, which are respectively deposited at the CGMCC under accession numbers CGMCC 15527 and CGMCC 15528.

According to the present disclosure, a ratio of a number of *Lactobacillus plantarum* TSP05, that of *Lactobacillus Fermentum* TSF331, and that of *Lactobacillus reuteri* TSR332 ranges from 1:0.3:0.3 to 1:3:3. In an exemplary embodiment, the aforesaid ratio is 1:0.6:0.6. In another exemplary embodiment, the aforesaid ratio is 1:1:1.

Since *Lactobacillus plantarum* TSP05 of the present disclosure has been verified to effectively lower blood uric acid levels through in vivo testing in human subjects, the applicant believes that *Lactobacillus plantarum* TSP05 has a high potential for alleviating disorders of uric acid metabolism.

Therefore, the present disclosure provides a method for alleviating a disorder of uric acid metabolism, which includes administering to a subject in need thereof a composition containing the aforesaid *Lactobacillus plantarum* TSP05.

Examples of the disorder of uric acid metabolism may include, but are not limited to, gout, hyperuricemia, uric acid nephrolithiasis, recurrent acute gouty arthritis, chronic gouty arthritis, joint deformities, uric acid nephropathy, and combinations thereof.

As used herein, the term "alleviating" or "alleviation" refers to at least partially reducing, ameliorating, relieving, controlling, treating or eliminating one or more clinical signs of a disease or disorder; and lowering, delaying, stopping or reversing the progression of severity regarding the condition or symptom being treated and preventing or decreasing the likelihood or probability thereof.

According to the present disclosure, *Lactobacillus plantarum* TSP05 may be live cells or dead cells, concentrated or non-concentrated, a liquid, a paste, a semi-solid, or a solid (e.g., a pellet, a granule, or a powder), and may be heat-inactivated, frozen, dried, or freeze-dried (e.g., may be in a freeze-dried form or spray/fluid bed dried form). In an exemplary embodiment, *Lactobacillus plantarum* TSP05 is in a freeze-dried form.

In certain embodiments, the composition may further include the aforesaid *Lactobacillus fermentum* TSF331 and *Lactobacillus reuteri* TSR332.

According to the present disclosure, a ratio of a number of *Lactobacillus plantarum* TSP05, that of *Lactobacillus fermentum* TSF331, and that of *Lactobacillus reuteri* TSR332 in the composition ranges from 1:0.3:0.3 to 1:3:3. In an exemplary embodiment, the aforesaid ratio in the composition is 1:0.6:0.6. In another exemplary embodiment, the aforesaid ratio in the composition is 1:1:1.

According to the present disclosure, the composition may be formulated as a food product using a standard technique well known to one of ordinary skill in the art. For example, the composition may be directly added to an edible material, or may be used to prepare an intermediate composition (e.g., a premix) suitable to be subsequently added to the edible material.

As used herein, the term "food product" refers to any article or substance that can be ingested by a subject into the body thereof. Examples of the food product may include, but are not limited to, milk powder, fermented milk, yogurt, butter, beverages (e.g., tea, coffee, etc.), functional beverages, flour products, baked foods, confectionery, candies, fermented foods, health foods, animal feeds, and dietary supplements.

In certain embodiments, the composition may be formulated as a pharmaceutical composition. The pharmaceutical composition may further include a pharmaceutically acceptable carrier, and may be made into a dosage form suitable for oral administration or parenteral administration using technology well-known to those skilled in the art.

Examples of the pharmaceutically acceptable carrier may include, but are not limited to, solvents, buffers, emulsifiers, suspending agents, decomposers, disintegrating agents, dispersing agents, binding agents, excipients, stabilizing agents, chelating agents, diluents, gelling agents, preservatives, wetting agents, lubricants, absorption delaying agents, liposomes, and the like. The choice and amount of the pharmaceutically acceptable carrier are within the expertise of those skilled in the art.

Examples of the dosage form for oral administration or parenteral administration include, but are not limited to, injections (e.g., a sterile aqueous solution or a dispersion), sterile powders, tablets, troches, lozenges, pellets, capsules, dispersible powders or granules, solutions, suspensions, emulsions, drops, syrup, elixirs, slurry, and the like.

As used herein, the term "administering" or "administration" means introducing, providing or delivering a predetermined active ingredient to a subject by any suitable routes to perform its intended function.

As used herein, the term "subject" refers to any animal of interest, such as humans, monkeys, cows, sheep, horses, pigs, goats, dogs, cats, mice, and rats. In certain embodiments, the subject is a human.

The dose and frequency of administration of the composition of the present disclosure may vary depending on the following factors: the severity of the illness or disorder to be treated, routes of administration, and age, physical condition and response of the subject to be treated. In general, the composition may be administered in a single dose or in several doses.

The present disclosure will be further described by way of the following examples. However, it should be understood that the following examples are intended solely for the purpose of illustration and should not be construed as limiting the present disclosure in practice.

EXAMPLES

General Experimental Materials:
1. Lactic acid bacterial (LAB) strains
A. *Lactobacillus plantarum* TSP05

*Lactobacillus plantarum* TSP05, which is disclosed in the applicant's Chinese Invention Patent Application Publication No. CN 111543639 A, has been deposited at the Bioresource Collection and Research Center (BCRC) of the Food Industry Research and Development Institute (FIRDI) (No. 331, Shih-Pin Rd., Hsinchu City 300, Taiwan) under an accession number BCRC 910855 since Nov. 2, 2018, and has also been deposited at the China General Microbiological Culture Collection Center (CGMCC) of Chinese Academy of Sciences, the Institute of Microbiology (No. 1, West Beichen Rd., Chaoyang District, Beijing 100101, China), under an accession number CGMCC 16710 since Nov. 5, 2018.

B. *Lactobacillus fermentum* TSF331

*Lactobacillus fermentum* TSF331, which is disclosed in CN 111543639 A, has been deposited at the BCRC of the FIRDI under an accession number BCRC 910815 since Jan. 18, 2018, and has also been deposited at the CGMCC of Chinese Academy of Sciences, the Institute of Microbiology, under an accession number CGMCC 15527 since Mar. 29, 2018.

C. *Lactobacillus reuteri* TSR332

*Lactobacillus reuteri* TSR332, which is disclosed in CN 111543639 A, has been deposited at the BCRC of the FIRDI under an accession number BCRC 910816 since Jan. 18, 2018, and has also been deposited at the CGMCC of Chinese Academy of Sciences, the Institute of Microbiology, under an accession number CGMCC 15528 since Mar. 29, 2018.

D. Comparative LAB Strains

The applicant isolated the following LAB strains for them to serve as comparative LAB strains:

(1) *Lactobacillus plantarum* Lp323

*Lactobacillus plantarum* Lp323 used in the following experiments was isolated from fermented vegetables by the applicant using BD Difco™ *Lactobacilli* MRS (De Man, Rogosa and Sharpe) Agar. Preliminary morphological characterization test showed that *Lactobacillus plantarum* Lp323 is heterofermentative facultative anaerobic, Gram-positive, non-motile, catalase negative, and non-spore forming, and exhibits optimal growth at 37° C.±1° C. it was found that when *Lactobacillus plantarum* Lp323 performs glucose metabolism, no gas is generated. The cells of *Lactobacillus plantarum* Lp323 are rod-shaped with square ends, and occur in pairs or short chains. Identification of *Lactobacillus plantarum* Lp323 was verified using analytical profile index (API) test and 16S ribosomal DNA analysis according to procedures known to those skilled in the art (data not shown).

(2) *Lactobacillus rhamnosus* L-85

*Lactobacillus rhamnosus* L-85 used in the following experiments was isolated from the feces of a healthy subject by the applicant using BD Difco™ *Lactobacilli* MRS Agar. Preliminary morphological characterization test showed that *Lactobacillus rhamnosus* L-85 is heterofermentative facultative anaerobic, Gram-positive, non-motile, catalase negative, and non-spore-forming, and exhibits optimal growth at 37° C.±1° C. It was found that when *Lactobacillus rhamnosus* L-85 performs glucose metabolism, no gas is generated. The cells of *Lactobacillus rhamnosus* L-85 are rod-shaped with oval ends, and occur singly or in short chains. Identification of *Lactobacillus rhamnosus* L-85 was verified using analytical profile index (API) test and 16S ribosomal DNA analysis according to procedures known to those skilled in the art (data not shown).

General Procedures:
1. High Performance Liquid Chromatography (HPLC) Analysis

In the following experiments, test samples containing various types of purines (i.e., guanosine, inosine, guanine, hypoxanthine and uric acid) were subjected to HPLC analysis using LC-20A liquid chromatography system (Manufacturer: Shimadzu Corporation) so as to determine concentrations thereof. The operating parameters and conditions for performing HPLC are summarized in Table 1 below. In comparison, different concentrations of guanosine, inosine, guanine, hypoxanthine and uric acid (purchased from Sigma-Aldrich), each serving as control standard, were also subjected to the HPLC analysis to prepare a standard curve.

TABLE 1

| | |
|---|---|
| Type of chromatography column | Cosmosil™ 5C18-AR-II (Manufacturer: Nacalai Tesque, Inc.) |
| Size of chromatography column | Length: 25 cm; inner diameter: 4.6 mm |
| Temperature of chromatography column | 25° C. |
| Injection volume of test sample | 50 μL |
| Mobile phase | 0.1 mM sodium perchlorate (NaClO$_4$)/0.187 M phosphoric acid (H$_3$PO$_4$) |
| Flow rate of test sample | 1.0 mL/min |
| Type of detector and detection wavelength | Photodiode array detector, 254 nm (Manufacturer: Hitachi, Ltd.; Model No.: L-2455) |

Example 1

Evaluation of the Effect of *Lactobacillus plantarum* TSP05 on Degradation of Purines In Vitro In order to evaluate the efficacy of *Lactobacillus plantarum* TSP05 on in vitro degradation of purines such as inosine and guanosine, the following experiments were conducted.

A. Preparation of Bacterial Suspension of LAB Strain

A respective one of the five LAB strains described in section 1 of the General Experimental Materials was inoculated into 5 mL of a BD Difco™ TN Lactobacilli MRS (De Man, Rogosa and Sharpe) broth (Catalogue no.: DF0881-17-5) supplemented with 0.05% (w/w) cysteine, and was then cultured at a temperature of 37° C. for 24 hours to obtain a respective one of LAB inoculums.

Thereafter, a respective one of the LAB inoculums was inoculated in an amount of 2% (v/v) into 5 mL of a *Lactobacilli* MRS broth, and was then cultured under an anaerobic condition at a temperature of 37° C. overnight to obtain a respective one of LAB cultures. Next, each of the LAB cultures was subjected to centrifugation at 4° C. under a speed of 3,000 rpm for 10 minutes to form a supernatant and a pellet. After that, the supernatant was poured off, and then the pellet was washed with an appropriate amount of 0.1 M phosphate-buffered saline (PBS), followed by resuspending the pellet in an appropriate amount of PBS, so as to obtain a bacterial suspension having a bacterial concentration of $1\times10^9$ CFU/mL, which was determined using a plate counting medium (Manufacturer: BD Difco™, USA). In the following experiments, a portion of the respective one of the resultant bacterial suspensions served as a single LAB group (i.e., a corresponding one of a single LAB experimental group and single LAB comparative groups 1 to 4), while another portion thereof was equally mixed at the same volume ratio with portions of other bacterial suspensions to form a mixture LAB group (i.e., a corresponding one of a mixture LAB experimental group and mixture LAB comparative groups 1 to 3), as shown in Table 2 below.

TABLE 2

| LAB group | Composition of bacterial suspension(s) |
|---|---|
| Single LAB experimental group | TSP05 |
| Single LAB comparative group 1 | Lp323 |
| Single LAB comparative group 2 | TSF331 |
| Single LAB comparative group 3 | TSR332 |
| Single LAB comparative group 4 | L-85 |
| Mixture LAB experimental group | TSP05, TSF331, TSR332 |
| Mixture LAB comparative group 1 | TSF331, TSR332 |
| Mixture LAB comparative group 2 | Lp323, TSF331, TSR332 |
| Mixture LAB comparative group 3 | TSF331, TSR332, L-85 |

Note:
each LAB group has the same total bacterial concentration (i.e., $1 \times 10^9$ CFU/mL)

B. Determination of Purine Concentration

Appropriate amounts of inosine (Manufacturer: Sigma-Aldrich; Catalogue No.: I4125) and guanosine (Manufacturer: Sigma-Aldrich; Catalogue No.: G6752) were added to each LAB group prepared in the abovementioned section entitled "A. Preparation of bacterial suspension of LAB strain", such that both of a final concentration of inosine and that of guanosine in each LAB group were 1.26 mM. Next, for each of the LAB groups, the degradation reaction was allowed to proceed under an anaerobic condition in a constant-temperature shaking incubator at 37° C. and 140 rpm for 30 minutes. Thereafter, 900 µL of the reaction mixture of the respective LAB group was taken out to be mixed with 100 µL of 0.1 M perchloric acid ($HClO_4$) so as to stop the reaction, followed by centrifugation to remove the bacterial cells. The resultant supernatant of the respective LAB group was subjected to filtration using a filter membrane having a pore size of 0.22 µm, followed by conducting HPLC analysis as described in section 1 of the General Procedures, so as to determine the concentrations of inosine and guanosine (i.e., residual purines).

The percentage of each of these residual purines in a respective one of the LAB groups was calculated by substituting the thus determined purine concentration after the aforesaid reaction into the following formula:

$$A = (1 - B/C) \times 100 \quad (1)$$

where A=percentage of residual purine
B=purine concentration after reaction (mM)
C=purine concentration before reaction (mM) (i.e., 1.26 mM)

The results are shown in Table 3 below.

TABLE 3

| | Percentage of residual purine (%) | |
|---|---|---|
| LAB group | Guanosine | Inosine |
| Single LAB experimental group | 53 | 44 |
| Single LAB comparative group 1 | 72 | 37 |
| Single LAB comparative group 2 | 49 | 41 |
| Single LAB comparative group 3 | 22 | 10 |
| Single LAB comparative group 4 | 94 | 96 |
| Mixture LAB experimental group | 0 | 0 |
| Mixture LAB comparative group 1 | 31 | 22 |
| Mixture LAB comparative group 2 | 46 | 28 |
| Mixture LAB comparative group 3 | 58 | 53 |

As shown in Table 3, in comparison with the single LAB comparative group 1, the percentage of residual inosine in the single LAB experimental group shows no significant difference, while the percentage of residual guanosine in the single LAB experimental group was significantly reduced, suggesting that *Lactobacillus plantarum*. TSP05 has an excellent guanosine degradation ability compared with other strains of *Lactobacillus plantarum* (e.g., Lp323).

In addition, the percentages of residual guanosine and inosine in the mixture LAB comparative group 1 were between those of the single LAB comparative group 2 and single LAB comparative group 3, indicating that the combined use of *Lactobacillus fermentum* TSF331 and *Lactobacillus reuteri* TSR332 did not produce a synergistic effect in degradation of purines. In contrast, the percentages of residual guanosine and inosine in the mixture LAB experimental group were significantly lower than those of the mixture LAB comparative group 1, single LAB experimental group, single LAB comparative group 2 and single LAB comparative group 3, suggesting that *Lactobacillus plantarum* TSP05 produces a synergistic effect in degradation of purines when used in combination with *Lactobacillus fermentum* TSF331 and *Lactobacillus reuteri* TSR332, which greatly improves the overall efficiency in purine degradation.

In order to verify these results, when the aforesaid supernatant of each LAB group was subjected to the HPLC analysis, the concentrations of guanine and hypoxanthine (which are metabolites of guanosine and inosine, respectively), as well as the concentration of uric acid (which is the final degradation product of purine metabolism), were also determined. The results are shown in Table 4 below.

TABLE 4

| | Concentration of purine metabolites (mM) | | |
|---|---|---|---|
| LAB group | Guanine | Hypoxanthine | Uric acid |
| Single LAB experimental group | 0.297 | 0.389 | 0 |
| Single LAB comparative group 1 | 0.149 | 0.577 | 0 |
| Single LAB comparative group 2 | 0.327 | 0.497 | 0 |
| Single LAB comparative group 3 | 0.830 | 0.754 | 0 |
| Single LAB comparative group 4 | 0 | 0 | 0 |
| Mixture LAB experimental group | 1.399 | 1.264 | 0 |
| Mixture LAB comparative group 1 | 0.989 | 1.067 | 0 |

TABLE 4-continued

| LAB group | Concentration of purine metabolites (mM) | | |
|---|---|---|---|
| | Guanine | Hypoxanthine | Uric acid |
| Mixture LAB comparative group 2 | 0.406 | 0.661 | 0 |
| Mixture LAB comparative group 3 | 0.201 | 0.173 | 0 |

As shown in Table 4, uric acid was not detected in each LAB group. In addition, there is an inverse correlation between the percentage of residual guanosine and residual inosine (see Table 3) and the amount of their respective metabolites, i.e., guanine and hypoxanthine. Moreover, it can be seen that *Lactobacillus plantarum* TSP05 shows significantly improved efficiency in degradation of purines as compared with other strains of *Lactobacillus plantarum*, and produces a synergistic effect in degradation of purines when used in combination with *Lactobacillus fermentum* TSF331 and *Lactobacillus reuteri* TSR332. These results show that *Lactobacillus plantarum* TSP05 has an excellent purine degradation ability, and is expected to have the potential for reducing purine content in edible materials, and can be further used in combination with *Lactobacillus fermentum* TSF331 and *Lactobacillus reuteri* TSR332 to enhance the effect of degrading purines.

Example 2

Evaluation of the Effect of *Lactobacillus plantarum* TSP05 on Lowering Blood Uric Acid Level In Vivo In order to evaluate the efficacy of *Lactobacillus plantarum* TSP05 on lowering of blood uric acid level in vivo, the following experiments were conducted.
Test Subjects:
125 test subjects participating in the following experiments are employees of Glac Biotech Co., Ltd., Taiwan, and their relatives and friends, including 66 men and 59 women aged between 18 and 65 years old whose blood uric acid concentrations range from 7 mg/dL to 8 mg/dL.
Experimental Materials:
A. Preparation of Bacterial Capsules of LAB Strain
A respective one of *Lactobacillus plantarum* TSP05, *Lactobacillus fermentum* TSF331 and *Lactobacillus reuteri* TSR332 described in section 1 of the General Experimental Materials was inoculated into 5 mL of a BD Difco™ Lactobacilli MRS broth, and was then cultured under an anaerobic condition at a temperature of 37° C. overnight to obtain a respective one of LAB cultures. After the number of bacteria was determined using a plate counting medium (Manufacturer: BD Difco™, USA), a respective one of the LAB cultures was subjected to a freeze-drying treatment so as to obtain a bacterial powder having a bacterial concentration of $1 \times 10^{11}$ CFU/g. In addition, portions of the bacterial powders of *Lactobacillus plantarum* TSP05, *Lactobacillus fermentum* TSF331 and *Lactobacillus reuteri* TSR332 were mixed together in a weight ratio of 1:0.6:0.6, so as to obtain a mixture LAB powder having a bacterial concentration of $1 \times 10^{11}$ CFU/g. Thereafter, a respective one of the bacterial powders of *Lactobacillus plantarum* TSP05, *Lactobacillus fermentum* TSF331 and Lactobacillus reuteri TSR332, and the mixture LAB powder was mixed with maltodextrin in a weight ratio of 2:3, and the respective mixture was then manufactured into bacterial capsules, each of which contained a total bacterial number of $2 \times 10^{10}$ CFU.
Experimental Procedures:
First, the 125 test subjects were randomly divided into 5 groups, i.e., a TSP05 group, a TSF331 group, a TSR332 group, a mixture LAB group and a control group (n=25 per group). The test subjects in the TSP05 group, TSF331 group, TSR332 group and the mixture LAB group were respectively orally administered with the bacterial capsules containing the *Lactobacillus plantarum* TSP05 powder, those containing the *Lactobacillus fermentum* TSF331 powder, those containing the *Lactobacillus reuteri* TSR332 powder, and those containing the mixture LAB powder in an administration frequency of 1 capsule per day for 60 days, while the test subjects in the control group were orally administered with capsules each containing 200 mg of maltodextrin at the same administration frequency and time period. Before the administration and on day 30 and day 60 after the start of the administration, the concentration of fasting blood uric acid of each test subject was determined using Easy-Touch GCU Blood Glucose/Cholesterol/Uric Acid Multi-Function Monitoring System (Model No: ET-301).
The relative blood uric acid level of the test subjects in each group was calculated by substituting the concentration of fasting blood uric acid thus determined before and after the start of administration into the following formula:

$$D = E/F \times 100 \qquad (2)$$

where D=relative blood uric acid level (%)
E=blood uric acid concentration determined on day 30 or day 60 after start of administration (mg/dL)
F=blood uric acid concentration before administration (mg/dL)
Results:
FIG. 1 shows the relative blood uric acid level of the test subjects in each group on day 30 and day 60 after the start of administration. As shown in FIG. 1, for each of the TSP05 group, TSF331 group, TSR332 group and the mixture LAB group, the relative blood uric acid level decreased on day 60 compared with that determined on day 30 after the start of administration. To be specific, in comparison with the TSP05 group, TSF331 group and TSR332 group, the mixture LAB group exhibited a significantly more decline of the relative blood uric acid level on day 60. This results demonstrate that Lactobacillus plantarum TSP05 is capable of effectively reducing blood uric acid level, and such effect can be enhanced when *Lactobacillus plantarum* TSP05 is used in combination with *Lactobacillus fermentum* TSF331 and *Lactobacillus reuteri* TSR332.

In summary, *Lactobacillus plantarum* TSP05, when used alone or in combination with *Lactobacillus fermentum* TSF331 and *Lactobacillus reuteri* TSR332, not only reduces purine content in edible materials in vitro so as to reduce purine intake, but also directly decreases blood uric acid level in vivo, hence being expected to be useful for alleviating disorders of uric acid metabolism.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A method for reducing blood uric acid level in a subject, comprising administering to the subject in need thereof a composition containing *Lactobacillus plantarum* TSP05, *Lactobacillus fermentum* TSF331 and *Lactobacillus reuteri* TSR332 which are respectively deposited at the China General Microbiological Culture Collection Center (CGMCC) under accession numbers CGMCC 16710, CGMCC 15527 and CGMCC 15528, wherein a ratio of a number of *Lactobacillus plantarum* TSP05, to that of *Lactobacillus fermentum* TSF331, and to that of *Lactobacillus reuteri* TSR332 is 1:0.6:0.6.

2. The method as claimed in claim 1, wherein the subject suffers from a disorder of uric acid metabolism selected from the group consisting of gout, hyperuricemia, uric acid nephrolithiasis, recurrent acute gouty arthritis, chronic gouty arthritis, joint deformities, uric acid nephropathy, and combinations thereof.

3. The method as claimed in claim 1, wherein the composition is formulated as a food product.

4. The method as claimed in claim 1, wherein the composition is formulated as a pharmaceutical composition.

5. The method as claimed in claim 4, wherein the pharmaceutical composition includes a pharmaceutically acceptable carrier.

6. The method as claimed in claim 4, wherein the pharmaceutical composition is in a dosage form for oral administration.

7. The method as claimed in claim 4, wherein the pharmaceutical composition is in a dosage form for parenteral administration.

8. A method for reducing purine content in an edible material that reduces blood uric acid level in a subject, comprising cultivating *Lactobacillus plantarum* TSP05, *Lactobacillus fermentum* TSF331 and *Lactobacillus reuteri* TSR332 which are respectively deposited at the China General Microbiological Culture Collection Center (CGMCC) under accession numbers CGMCC 16710, CGMCC 15527 and CGMCC 15528, and which are capable of degrading a purine in the edible material, wherein a ratio of a number of *Lactobacillus plantarum* TSP05, to that of *Lactobacillus fermentum* TSF331, and to that of *Lactobacillus reuteri* TSR332 is 1:0.6:0.6.

* * * * *